US00PP26803P2

(12) United States Plant Patent
Visser et al.

(10) Patent No.: US PP26,803 P2
(45) Date of Patent: Jun. 7, 2016

(54) ***JUNIPERUS* PLANT NAMED 'LITTLE JOANNA'**

(50) Latin Name: *Juniperus squamata*
Varietal Denomination: Little Joanna

(71) Applicants: Eddy Visser, Lippenhuizen (NL); Jeroen Visser, Lippenhuizen (NL)

(72) Inventors: Eddy Visser, Lippenhuizen (NL); Jeroen Visser, Lippenhuizen (NL)

(73) Assignee: Gebroeders Visser., Lippenhuizen (NL)

( * ) Notice: Subject to any disclaimer, the term of this patent is extended or adjusted under 35 U.S.C. 154(b) by 111 days.

(21) Appl. No.: 14/121,413

(22) Filed: Sep. 3, 2014

(51) Int. Cl.
*A01H 5/00* (2006.01)

(52) U.S. Cl.
USPC ..... Plt./214

(58) Field of Classification Search
USPC ..... Plt./214
See application file for complete search history.

(56) References Cited

PUBLICATIONS

PLUTO Plant Variety Database Feb. 9, 2016. p. 1.*

* cited by examiner

*Primary Examiner* — Annette Para
(74) *Attorney, Agent, or Firm* — Penny J. Aguirre

(57) ABSTRACT

A new cultivar of *Juniperus squamata* named 'Little Joanna' that is characterized by its very compact, well-branched and creeping plant habit, its foliage that is intense steel blue in color, and its average height of about 15 cm and an average spread of 75 cm when mature.

2 Drawing Sheets

Botanical classification: *Juniperus squamata.*
Varietal denomination: 'Little Joanna'.

BACKGROUND OF THE INVENTION

The present invention relates to a new and distinct cultivar of *Juniperus squamata* and will be referred to hereafter by its cultivar name, 'Little Joanna'. 'Little Joanna' is a new cultivar of juniper, an evergreen shrub grown for use as an ornamental landscape plant.

The Inventors discovered the new cultivar in June of 2003 as a naturally occurring branch mutation of *Juniperus squamata* 'Blue Carpet' (not patented) that was growing in a container at their nursery in Lippenhuizen, The Netherlands.

Asexual propagation of the new cultivar was first accomplished by one of the Inventors using semi-hardwood cuttings in 2003 in Lippenhuizen, The Netherlands. Asexual propagation by semi-hardwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Little Joanna' as a unique cultivar of *Juniperus*.

1. 'Little Joanna' exhibits a very compact, well-branched and creeping plant habit.
2. 'Little Joanna' exhibits foliage that is intense steel blue in color.
3. 'Little Joanna' exhibits an average height of about 15 cm and an average spread of 75 cm when mature.

The parent plant, 'Blue Carpet', differs from 'Little Joanna' in having a less compact plant habit, less dense branching, and foliage color that is less intense and grey-blue. In addition, 'Little Joanna' can be compared to *Juniperus procumbens* cultivar 'Nana' (not patented) and *Juniperus squamata* cultivar 'Blue Star' (not patented). 'Nana' is similar to 'Little Joanna' in foliage coloration and in having a creeping plant habit, but differs from 'Little Joanna' in having a less compact and less branched plant habit, in having foliage coloration that is less intense, and in being taller in height. 'Blue Star' is similar to 'Little Joanna' in foliage coloration, but differs from 'Little Joanna' in having a less creeping plant habit.

BRIEF DESCRIPTION OF THE DRAWINGS

The accompanying colored photographs illustrate the overall appearance and distinct characteristics of the new *Juniperus*. The photographs were taken of a plant nine months in age as grown outdoors in a 13-cm container in Lippenhuizen, The Netherlands.

The photograph in FIG. 1 provides a side view of 'Little Joanna' and illustrates its plant habit.

Figure 1:
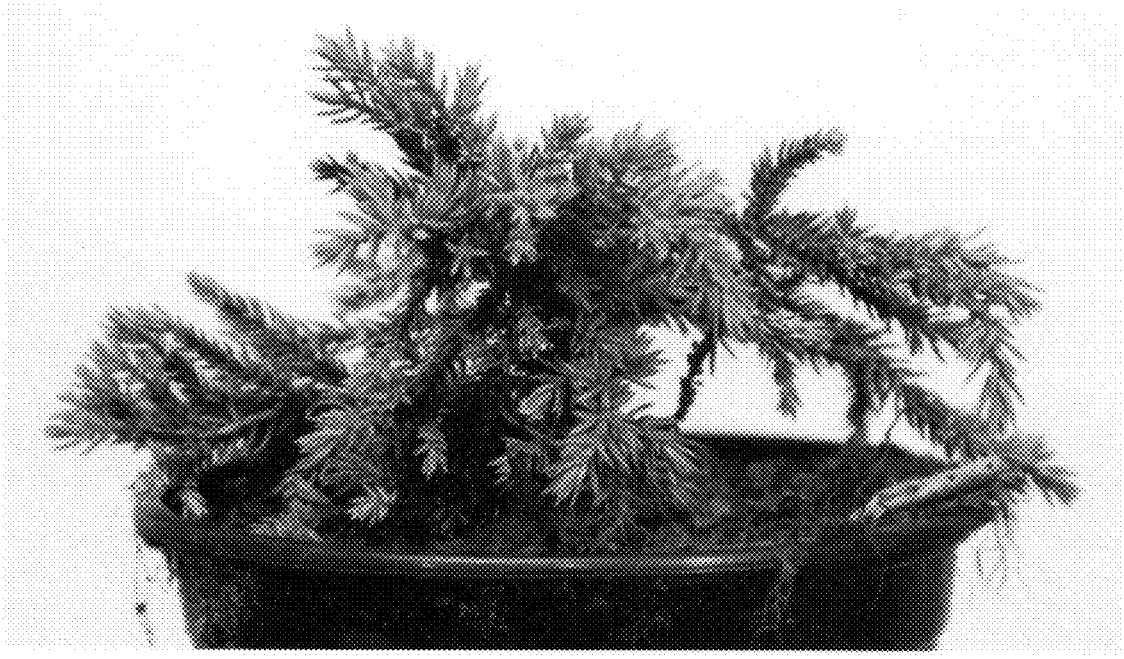
Figure 2:
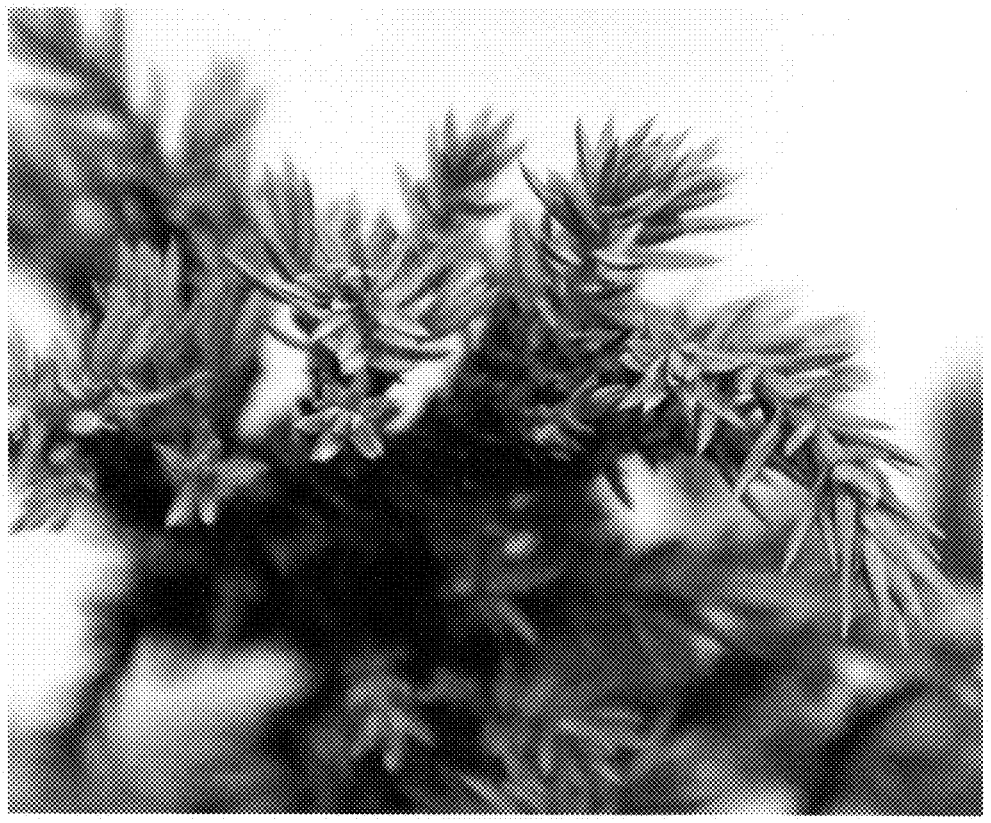

The photograph in FIG. 2 provides a close-up view of the foliage of 'Little Joanna'.

The colors in the photographs are as close as possible with the photographic and printing technology utilized and the color values cited in the detailed botanical description accurately describe the colors of the new *Juniperus*.

DETAILED BOTANICAL DESCRIPTION

The following is a detailed description of the new cultivar as taken from nine month-old plants grown outdoors in 13-cm containers in Lippenhuizen, The Netherlands with average day temperatures ranging from 10° to 20° C. and average night temperatures ranging from 1° to 12° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.

*Plant habit.*—Compact, well-branched and creeping plant habit.

*Height and spread.*—An average of 7.8 cm in height and 15.7 cm in width in a 13-cm container, matures in the landscape to an average of 15 cm in height and 75 cm in spread.

*Plant shape.*—Flattened to low flattened globular shape.

*Cold hardiness.*—At least to U.S.D.A. Zone 5.

*Diseases and pests.*—No particular resistance and susceptibility to diseases or pests have been observed to date.

*Root description.*—Fibrous.

*Growth rate.*—Moderate.

*Propagation.*—Semi-hardwood cuttings.

Stem description:

*Stem shape.*—Rounded.

*Stem size.*—Average of 7.8 cm in length and 2 mm in diameter.

*Stem surface.*—Glabrous and matte when young and bark is flaky when mature.

*Branching.*—Main stems grow from base and have an average of 9 lateral branches.

*Stem aspect.*—Very strong, held at an average angle of 80° to main stem.

*Internode length.*—Average of 1 mm.

*Stem color.*—Young stems; N138C, mature bark, 200B.

Foliage description:

*Leaf arrangement.*—Opposite.

*Leaf attachment.*—Sessile.

*Leaf shape.*—Lanceolate, scale-like.

*Leaf division.*—Simple.

*Leaf base.*—Cuneate.

*Leaf apex.*—Sharply pointed and moderately sharp to the touch.

*Leaf venation.*—Not distinguishable.

*Leaf stomata.*—Two present on lower surface divided by the rib, color 115D.

*Leaf margins.*—Entire.

*Leaf fragrance.*—When crushed, the foliage produces a strong pleasant smell.

*Leaf surface.*—Upper and lower surfaces; waxy, glabrous and matte.

*Leaf color.*—Young upper surface; 122C, young lower surface; 143A to 143B, mature upper surface; 137B and slightly tinged with 122B, mature lower surface; 137C.

*Leaf size.*—An average of 6 mm in length and 1.8 mm in width.

*Leaf quantity.*—Average of 600 scale-like leaves per lateral branch.

Inflorescence description: No flowers have been observed to date.

Fruit and seed description: No cones or seeds have been observed to date.

It is claimed:

1. A new and distinct cultivar of *Juniperus* plant named 'Little Joanna' as herein illustrated and described.

* * * * *